United States Patent [19]

Fay et al.

[11] Patent Number: 5,314,497
[45] Date of Patent: May 24, 1994

[54] APPARATUS AND METHOD FOR SEALING A LINER TO A PROSTHESIS

[76] Inventors: John N. Fay; Cheryl A. Fay, both of 1120 Boca Ciega Isle, St. Petersburg Beach, Fla. 33706

[21] Appl. No.: 901,319

[22] Filed: Jun. 19, 1992

Related U.S. Application Data

[63] Continuation-in-part of Ser. No. 814,969, Dec. 23, 1991, abandoned.

[51] Int. Cl.⁵ .............................................. A61F 2/80
[52] U.S. Cl. ........................................ 623/34; 623/33; 623/37
[58] Field of Search ............... 623/34, 33, 36, 37, 623/35

[56] References Cited

U.S. PATENT DOCUMENTS

| | | | |
|---|---|---|---|
| 1,893,853 | 1/1933 | Tullis | 623/37 |
| 2,634,424 | 1/1953 | O'Gorman | 623/37 |
| 2,696,011 | 12/1954 | Galdik | 623/33 |
| 3,309,714 | 3/1967 | Porten | 623/37 |
| 3,784,988 | 1/1974 | Trumpler | 623/35 |

FOREIGN PATENT DOCUMENTS

| | | | |
|---|---|---|---|
| 0019612 | 11/1980 | European Pat. Off. | 623/37 |
| 0086147 | 8/1983 | European Pat. Off. | 623/36 |
| 2712342 | 9/1977 | Fed. Rep. of Germany | 623/35 |
| 2345138 | 1/1977 | France | 623/34 |

*Primary Examiner*—Randall L. Green
*Assistant Examiner*—D. Willse
*Attorney, Agent, or Firm*—Joseph C. Mason, Jr.; Ronald E. Smith

[57] ABSTRACT

A liner that covers an amputation stump and which cushions the stump when it is placed into a prosthesis socket includes selectively inflatable bladders for customizing the liner to fit individual patients. In a first embodiment, the liner is made of two liner parts, one being an inner liner and the other being an outer liner. The inner liner is placed onto the amputation stump and a prosthetist determines the region or regions where bladders are needed to provide a comfortable fit. The region or regions are outlined with an adhesive and the outer liner is then brought into overlying relation to the inner liner so that the two liner parts adhere to one another along the outlined regions. Upon inflation, the inner liner conforms to the shape of the amputation stump to provide enhanced cushioning and the outer liner conforms to the shape of the interior wall of the socket and the patient receives a custom fit from a simple appliance. An annular bladder at the proximal rim of the socket creates a substantially perfect seal to maintain the suction within the socket. In a second embodiment, a tubular cuff replaces the outer liner and a triple seal is achieved when the socket is inserted between the cuff and the inner liner. In a third embodiment, an annular return bend is formed in the inner liner so that the cuff is integral with it.

12 Claims, 6 Drawing Sheets

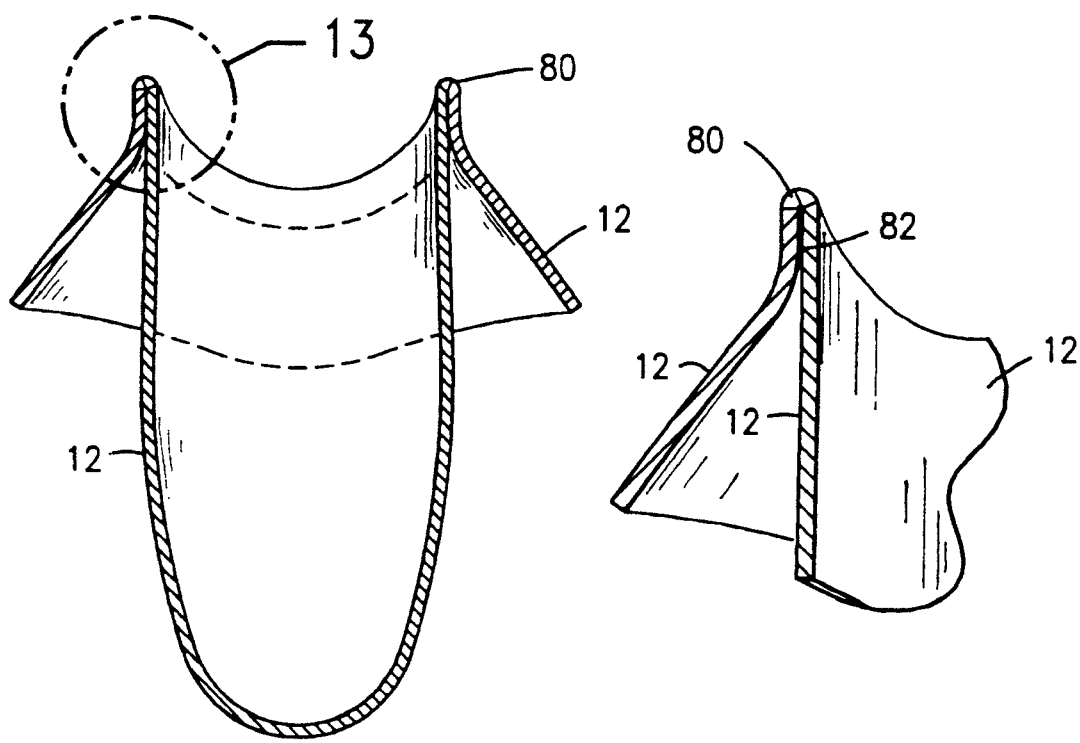
Fig. 12
Fig. 13
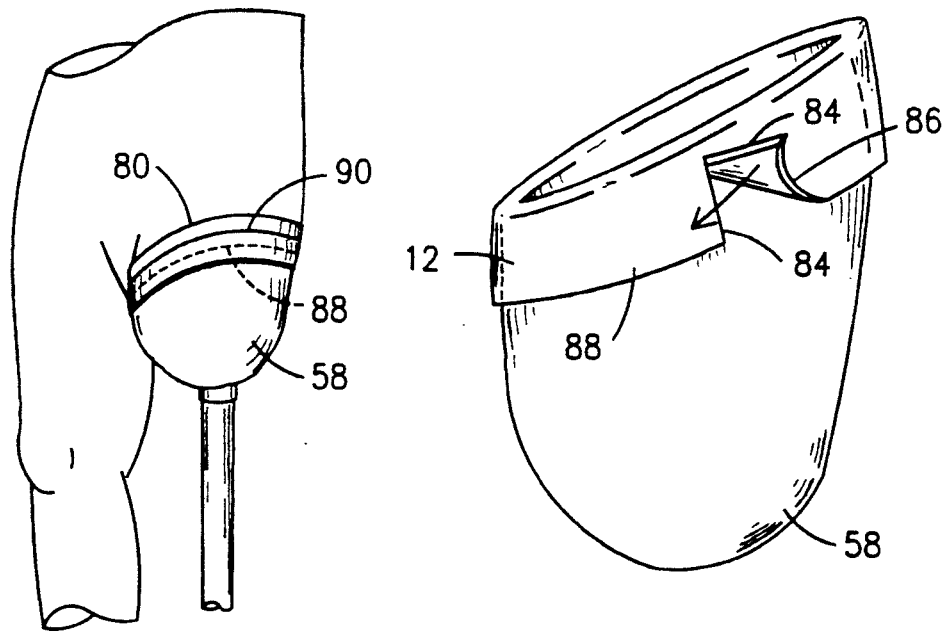
Fig. 14
Fig. 15

APPARATUS AND METHOD FOR SEALING A LINER TO A PROSTHESIS

This is a continuation-in-part of copending application Ser. No. 07/814,969 filed on Dec. 23, 1991, now abandoned.

TECHNICAL FIELD

This invention relates, generally, to prostheses. More particularly, it relates to a liner that cushions an amputation stump received within a hard socket.

CROSS-REFERENCE TO RELATED DISCLOSURES

This continuation-in-part disclosure relates to a copending disclosure of the same title by the same inventor, filed Dec. 23, 1991, Ser. No. 07/814,969, now abandoned.

BACKGROUND ART

The crudest form of a prosthesis is a hard, stump-receiving socket. If a socket is for receiving the stump of a below-the knee amputee, it will be attached by suitable means to a prosthetic foot; if it is for an above-the knee amputee, it will be attached to a prosthetic knee as well. In either application, the amputee will experience discomfort arising from contact between the stump and the hard interior of the stump-receiving socket unless an adequate cushioning means is provided. Moreover, the socket will separate from the stump unless an attachment means is provided.

Some prosthetic devices are held onto the residual limb (amputation stump) by suction. When the residual limb is fully inserted, usually with the aid of a sock, the tissue is pulled slightly downwardly, by pulling on the sock, and this creates a suction within the socket that holds it on. Obviously, this suction must be maintained if the socket is to remain in place; this is accomplished by a check valve. It is equally obvious that a socket equipped with a check valve is more expensive than a socket without such a valve.

Another socket attachment method intended to make the downward pulling on the tissue easier includes the use of a cream-like material. A predetermined quantity of the cream is applied to the residual limb and said residual limb is then inserted into the socket. Although this method works, it is messy; the cream often soils the amputee's clothing, for example.

Some individuals fit socks over their residual limb in an attempt to make the prosthesis more comfortable. Several layers of socks will form a reasonably soft cushion, but there are a number of drawbacks to the use of socks as socket liners. Perhaps the most obvious limitation is the inability of socks to protect a particular point or area where extra cushioning is needed, i.e., socks provide the same amount of cushioning everywhere. Moreover, the diameter of a stump will vary during the day, especially where the amputee is active. Specifically, most stumps shrink in size as the day progresses because walking and other activities drives fluids out of the stump; this results in the need for more layers of socks and that need requires the amputee to travel throughout the day with a supply of extra socks on hand. It is also troublesome and time-consuming to remove the socket, add a layer or two of socks, and to reattach the socket several times per day. Amputees who use socks as cushioning means are of course familiar with other drawbacks not mentioned herein.

Perhaps even more problematic than daily stump volume variations are the long term variations brought about by long term weight loss or weight gain.

In response to the limitations of socks as a means for cushioning, inventors have developed a number of alternatives thereto. Perhaps the simplest, most obvious alternative is to line the socket with a cushioning means. The problem with cushioned stump-receiving sockets is equally obvious, i.e., the fit between the socket and the stump becomes loose as the day progresses, and the amputee must again resort to the expedient of employing multiple layers of socks to maintain a reasonably tight fit as required.

Cushioned sockets, like socks, also fail to provide extra cushioning to particular points or areas.

Accordingly, customized cushioning means have been developed so that each individual amputee may have a cushioning means that matches the contour of his or her residual limb. A cast is made of the stump by wrapping plaster bandages around it, or by simply inserting the stump into a vat of impressionable material. The negative of the stump thereby created is then filled with plaster or other suitable material; this produces a replica of the residual limb. A liner is then fabricated that provides the proper amount of cushioning at the places where extra cushioning is needed.

Although liners so fabricated are superior in performance to socks and non-customized liners, they do not compensate for the changes in size of the stump during a day or from day to day. Moreover, such liners are expensive because they must be made for one patient at a time.

In an attempt to provide customized liners that compensate for changes in stump size, inventors have developed liners that include inflatable bladders. Thus, as the day progresses, more air is introduced into preselected bladders to maintain the tight fit between the socket and stump and to maintain the amputee's comfort level.

Even these advanced liners have shortcomings. Their primary drawback is that they must be customized with a high degree of precision for each patient. Thus, they cannot be mass produced and their unit cost is therefore quite high.

For example, in U.S. Pat. No. 4,923,475 to Gosthnian et. al., the stump-engaging surface of each bladder is molded to have a shape conforming to the outer surface of the amputee's stump when the stump is under static pressure, i.e., the patient stands to place static pressure on the stump, and the bladders are made so that they conform, when deflated, to the particular contour of the stump thereby produced. This highly exacting procedure does not lend itself to mass production.

U.S. Pat. No. 4,923,474 to Klasson et. al. eschews bladders and discloses a liner that has a distal end that is highly elastic in a radial direction so that it tightly and snugly engages the stump as the stump changes size, yet which is substantially inelastic axially so that it will not stretch with the weight of a prosthesis.

In summary, even though the art of prosthetics is old and well-developed, it is still unsatisfactory in several major respects. Specifically, the art has failed to produce a highly effective yet simple means for providing a suction that prevents inadvertent separation of limb and socket, and it has failed to produce a cushioning means that can be easily adapted to fit an individual. Significantly, at the time the present invention was made, the art neither taught nor suggested to those of ordinary skill how the limitations of the prior art devices could be overcome.

DISCLOSURE OF INVENTION

The present invention pioneers the art of mass-produced, low unit cost prosthetic liners having bladders that may be customized to fit the individual user. The novel liners provide a facile means for compensating for daily and long-term fluctuations in stump volume.

This invention also provides the world's first effective means for maintaining a socket on a residual limb in the absence of check valves, cream-like substances, and other known suction-creating means such as single-suction sleeves of the type commonly made of latex, neoprene, and other suitable materials.

In a first embodiment, the novel liner obviates the need to make a negative of the patient's amputation stump, yet produces a liner having bladders that precisely conform to the stump and to the interior surfaces of the stump-receiving socket. Each bladder may be provided with a pump so that its degree of inflation may be adjusted as needed.

The insight behind this breakthrough in the art of liners having bladders is the discovery that bladders can be formed by placing two liners of equal size in nested relation to one another. Individual bladders are formed by applying a suitable adhesive to the interior liner, outlining the area where the bladder will be. The interior liner is then inserted into the outer liner and the adhesive joins the two liners along the extent of said adhesive, thereby forming a pocket or bladder. In this manner, the inner and outer liners can be manufactured in large quantities to reduce their unit cost, yet each individual user can have the liner customized by his or her prosthetist. More particularly, the prosthetist observes the stump when the interior liner is placed thereon, and marks the areas where bladders are needed. The adhesive is then applied to the inner liner and the outer liner is placed thereover. Alternatively, the prosthetist could apply the adhesive where needed, skipping the marking step.

Air is introduced into or released from each individual bladder by conventional valve means.

An annular bladder may be provided at the uppermost end thereof to form an airtight seal with the proximal end of the socket.

In the second embodiment, the outer liner may or may not be used and use of bladders is optional as well. Thus, the second embodiment addresses the longstanding but heretofore unresolved problem of limb and socket separation. It provides the world's first dual suction means and the dual suction is achieved in the absence of check valves or creams. In lieu of the full length, closed end outer liner of the first embodiment, the second embodiment employs a tubular cuff that overlies the inner liner and which is adhered thereto. More particularly, the cuff and inner liner are adhered to one another along their respective uppermost edges only. Thus, the body of the cuff and its lowermost edge are not attached to the inner liner. However, due to the elasticity of the cuff, it tightly overlies the inner liner. To attach the socket to the residual limb, the inner liner and cuff are first placed on the limb. The lower edge of the cuff is then either rolled up or pulled away from the inner liner so that the limb and inner liner may be fully inserted into the socket. The cuff is then rolled down or released into overlying relation to the socket, and the novel dual suction is thereby formed. The first suction is between the limb and the inner surface of the inner liner; the second suction is between the inner surface of the cuff and the outer surface of the socket. The residual limb is removed from the socket by breaking the second suction, i.e., by rolling up the cuff to a point above the proximal rim of the socket or by pulling the lowermost edge of the cuff radially away from the socket so that air can flow into the space above said proximal rim. In other words, the second suction is broken by reversing the steps required to create it.

In a third embodiment, the cuff is not a separate part; instead, the cuff is created by reversely turning the open upper end of the liner, i.e., by folding the top end of the liner back to create a cuff that is integrally formed with the liner. This avoids the need to fabricate a separate cuff and to adhere it to the liner.

An important object of this invention is to substantially reduce the cost of prosthetic liners while simultaneously providing an advanced liner that is easily customized to fit individual users with a high degree of comfort.

Another related object is to provide such a liner having inflatable bladders to accommodate short and long term changes in stump size without loss of suction.

Still another major object is to provide a suction-creating apparatus that is free of check valves and creams.

Moreover, a primary object is to provide the world's first dual-suction means for holding a socket onto a residual limb.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 12 is a front sectional view of the third embodiment, showing the inner liner reversely folded to create a cuff that is integral therewith;

FIG. 13 is an enlarged view of the area 13 circumscribed in FIG. 12;

FIG. 14 is a perspective view showing a fit where the medial side of the prosthesis is of a different elevation than the lateral side thereof; and FIG. 15 is a perspective view of how the liner of the third embodiment may be cut if needed to fit a prosthesis of the type shown in FIG. 14.

Similar reference numerals refer to similar parts throughout the several views of the drawings.

BEST MODES FOR CARRYING OUT THE INVENTION

Figure 1:
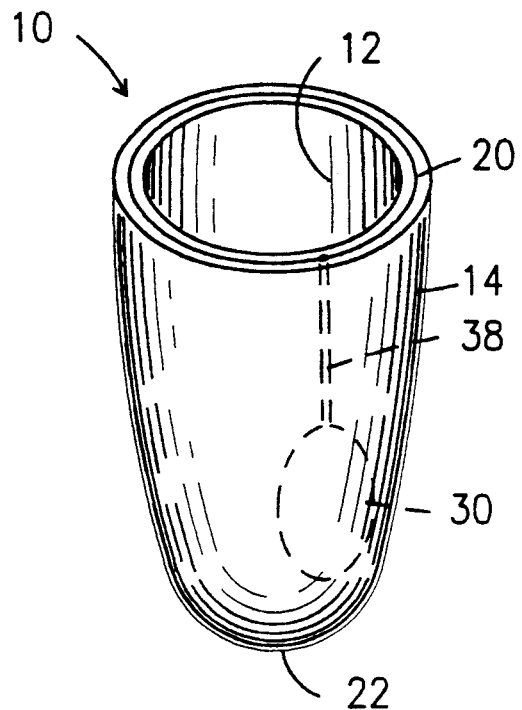
FIG. 1 is a perspective view of an assembled liner, showing a passageway for air to a bladder.

Referring now to FIG. 1, it will there be seen that a first embodiment of the invention is denoted as a whole by the reference numeral 10.

Liner means 10 includes an inner liner 12 and an outer liner 14, both of which are formed of the same material. The preferred material is silicone having a high degree of elasticity. Empirical tests have shown that a silicone compound having an elasticity of about twelve hundred percent is an ideal material.

Figure 2:
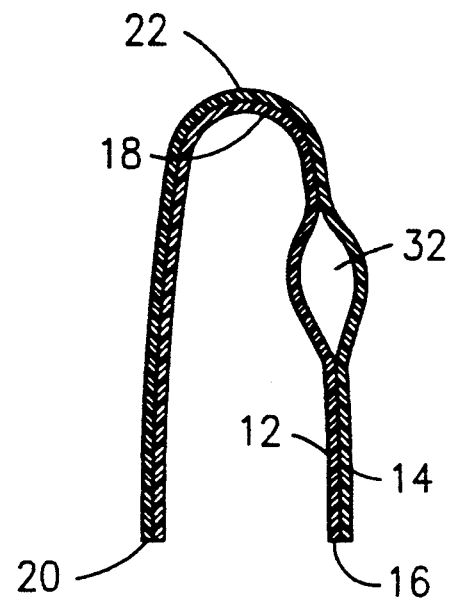
FIG. 2 is a sectional view showing the inner and outer liners in their nested configuration and showing a bladder in an inflated condition.

Inner liner 12 has a proximal open end 16 and a closed distal end 18 (FIG. 2); the diameter of the open end is greater than the diameter of the closed end so that the liner has a generally frustoconical appearance when viewed in side elevation, thereby matching the contour of a typical residual limb. Similarly, outer liner 14 has a proximal open end 20 and a closed distal end 22, and the former end has a greater diameter than the latter. The predetermined diameter of the open end 20 of our liner 14 may be greater than the predetermined diameter of the open end 16 of inner liner 12, and the same relationship may apply as between the respective closed ends 18 and 22. More particularly, the difference in diameter is substantially equal to the thickness of the inner liner 12. Accordingly, the second or outer liner 14 may fully receive the first or inner liner 12 as depicted in FIG. 2 and other FIGS. Alternatively, the two liners may have the same size; the outer liner may be rolled onto the inner liner and the uppermost edge of the inner liner may be trimmed off for aesthetic purposes. Where no bladders are to be formed, the inner liner may simply be slipped into the outer.

Figure 3:
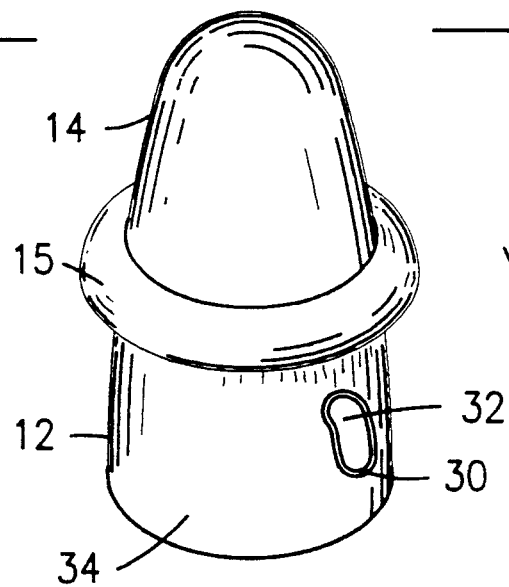
FIG. 3 is a perspective view showing a method for facilitating assembly of the novel liner.

To prepare the liner for use by the patient, inner liner 12 is first placed in overlying relation to the amputation stump by first rolling it inside out and then unrolling it onto the stump, or by any other suitable technique. The physician or prosthetist then observes the liner and residual limb carefully, and notes where bladders will be needed. Those areas where a bladder will be needed, in the professional opinion of the fitter, are circled with a pen or other suitable marker. A silicone adhesive 30 (FIG. 3), preferably made of the same material as the inner and outer liners, is then applied along the marked lines, and the second or outer liner 14 is placed into overlying relation to the inner liner 12. This may be accomplished in the same manner as used to fit the inner liner over the stump, i.e., the second liner is simply rolled up, inside out, and then unrolled onto the inner liner; this unrolling action is depicted in FIG. 3. In that FIG., the unrolled part of outer liner 14 is denoted 15; it is being unrolled in the direction indicated by directional arrow 17. Adhesive 30 may smear to some extent, but not to a significant extent. The circumscribed area 32 or areas are separated or demarcated from the areas 34 (FIG. 3) not circumscribed when the adhesive dries, as perhaps best depicted in FIG. 2; such circumscribed areas become the bladders when a pump means is employed to introduce air thereinto, as perhaps best depicted in FIGS. 1 and 4.

Figure 4:
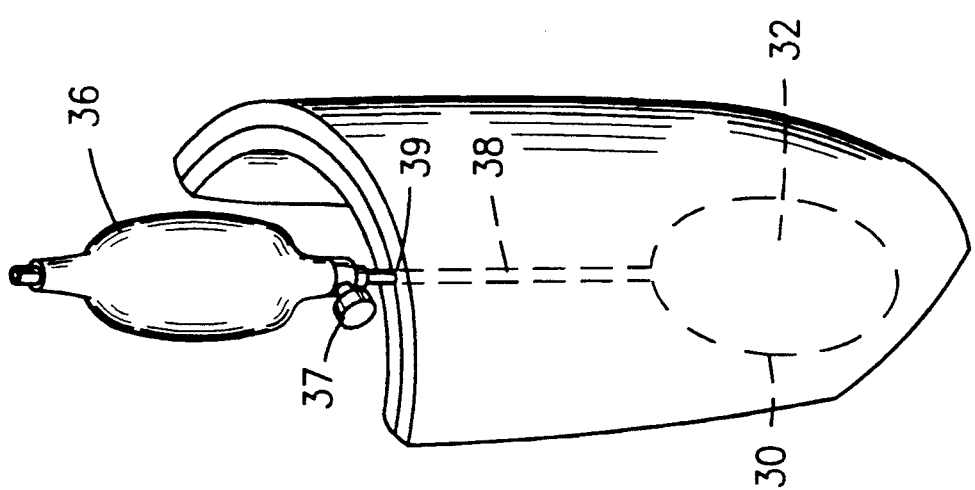
FIG. 4 is a perspective view of an assembled liner, in broken away form, showing a pump means for introducing and removing air into and from the bladder, respectively.

A suitable pump means is denoted 36 in FIG. 4; it includes a bulbous, flexible main body and a valve means 37. Passageway 38 interconnects bladder 32 and said pump 36. A check valve at the uppermost end of passageway 38 prevents flow of air out of bladder 38 when pump 36 is disconnected therefrom; stem 39 of pump 36 opens the check valve when the pump is in use as depicted in FIG. 4.

Figure 5:
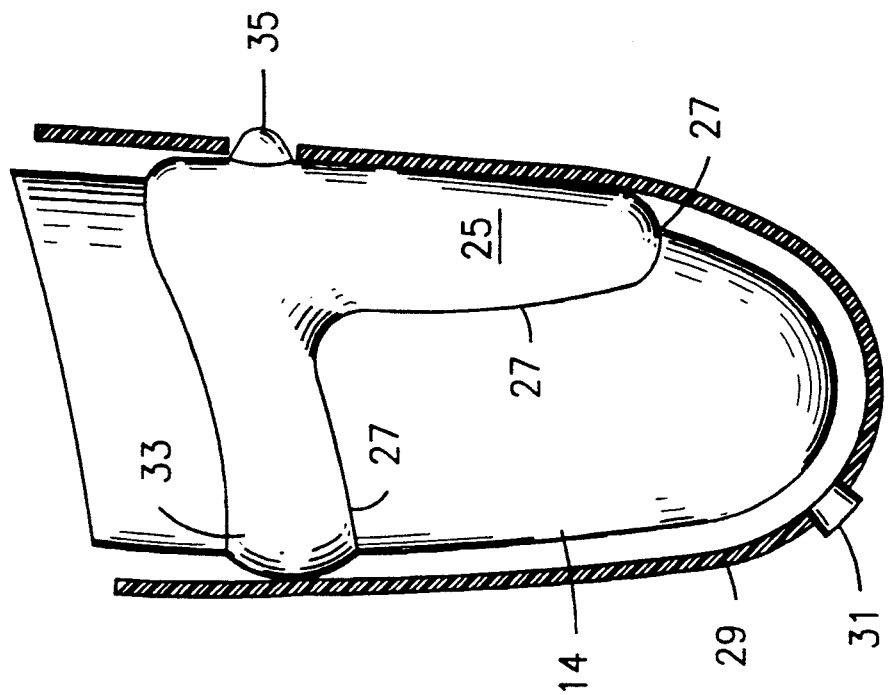
FIG. 5 is a side elevational view showing an embodiment having an annular bladder near the uppermost end of the liner and an integral bladder that depends therefrom.

It is also possible to place the air valve directly into the bladder, thereby eliminating any need for a passageway; such a valve is shown in FIG. 5. Valve 35 is in open fluid communication with annular bladder 33; said annular bladder provides a seal that prevents loss of the vacuum achieved when air in socket 29 escapes therefrom through check valve 31 when the residual limb is inserted into said socket 29. Reference numeral 27 indicates the elongate seal established between the inflated annular bladder 33 and bladder 25 which is integral therewith and which depends therefrom, and the inner surface of socket 29. The extent of the seal greatly enhances the ability of the novel construction to maintain the vacuum therewithin. The space between outer liner 14 and socket 29 is greatly exaggerated in FIG. 5 to better depict the bladder.

Figure 6:
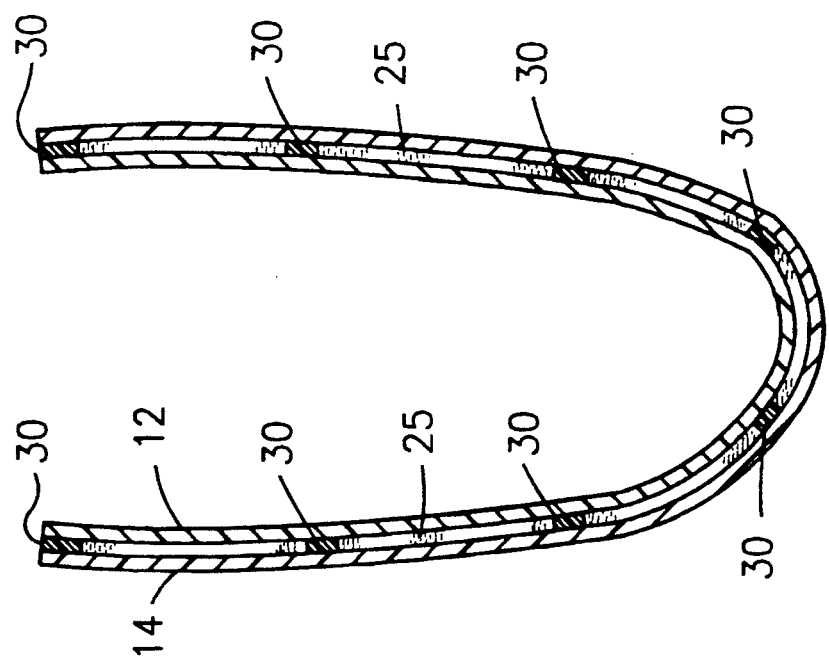
FIG. 6 is a sectional view showing how lubricant positioned between the inner and outer liners reduces friction on the patient's skin.

Areas that are not inflated, i.e., areas outside the adhesive borders, may be injected with a liquid or dry lubricant 23 (FIG. 6) which allows each liner to slide with respect to the other; this reduces friction to the skin.

Figure 8:
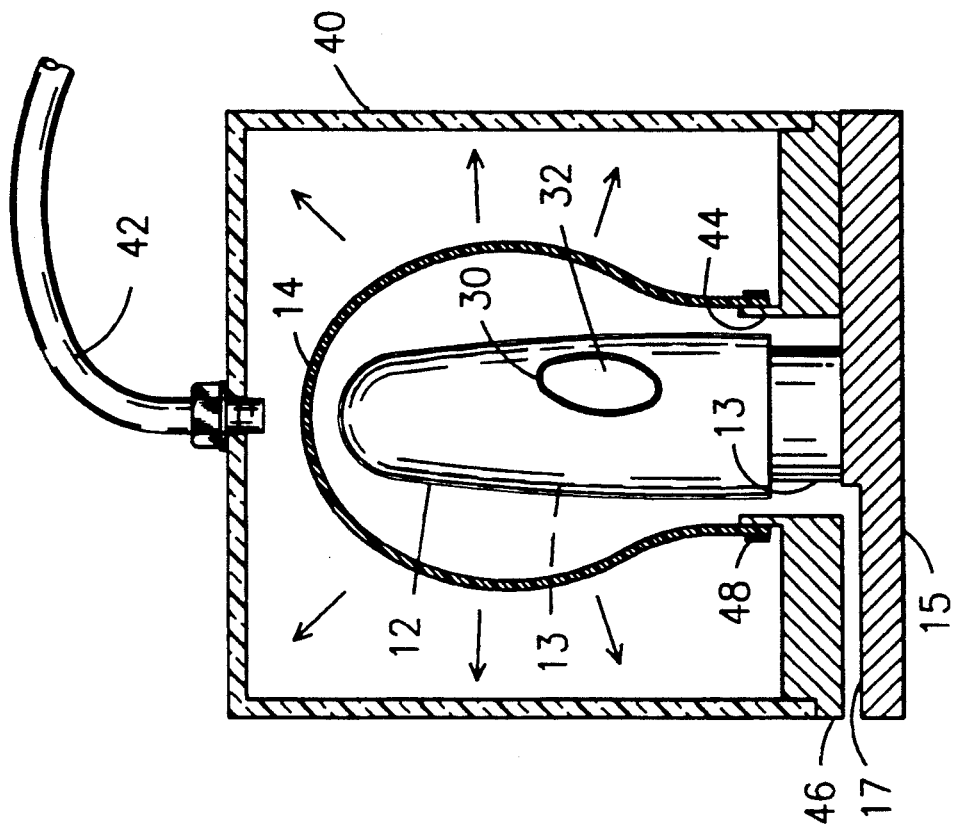
FIG. 8 is a sectional view showing the parts of FIG. 7 in their assembled configuration and showing an additional part.
Figure 7:
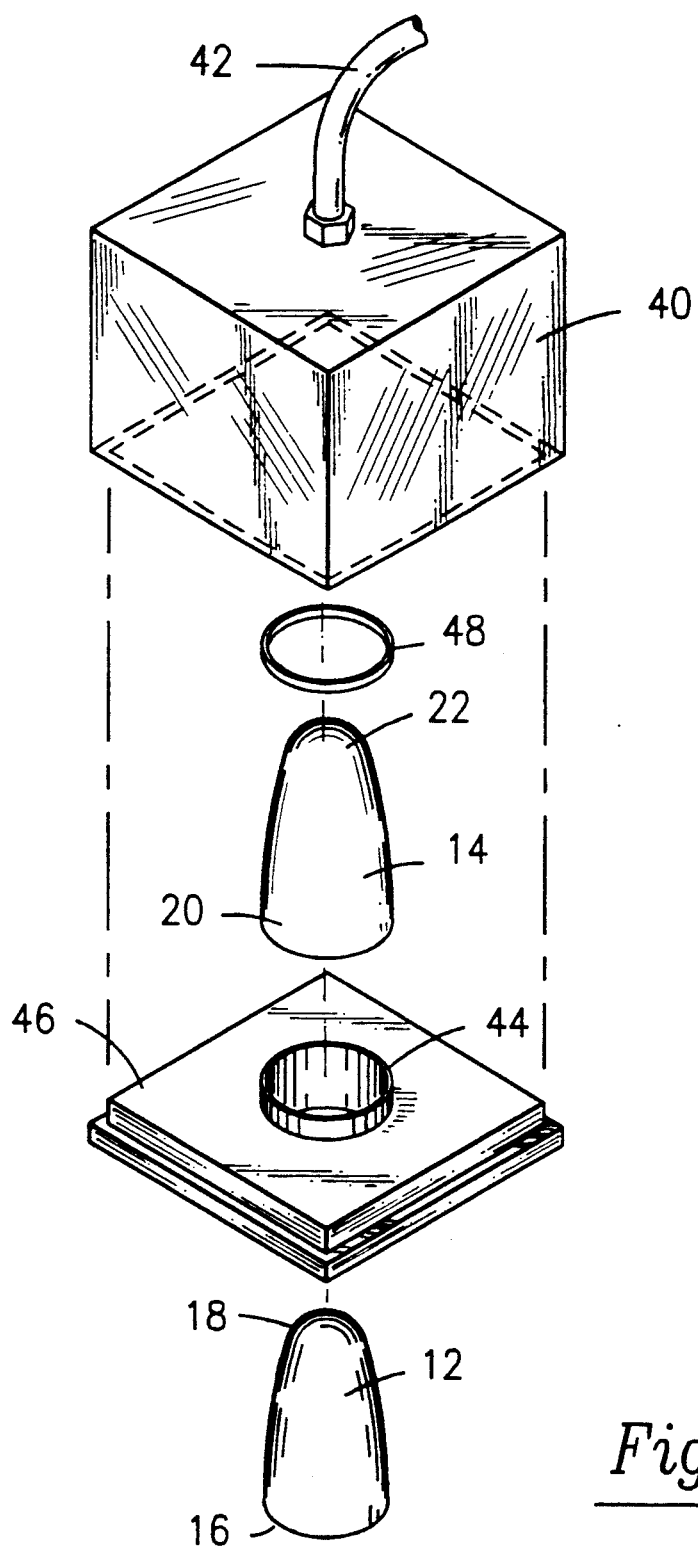
FIG. 7 is an exploded perspective view of the novel liner and an apparatus for facilitating its assembly.

An alternative method of placing the outer liner 14 over the inner liner 12 is depicted in FIGS. 7 and 8. A vacuum chamber 40 is connected to a suitable source of negative pressure, not shown, through a vacuum hose 42. A rim means 44 is positioned in a preselected wall 46 of the chamber 40, and the open proximal end 20 of the outer liner 14 is stretched and placed around said rim as shown in FIG. 8. A retainer ring 48 is positioned around open end 14 to hold it onto rim means 44. The source of negative pressure is then activated, and the resulting loss of pressure in the vacuum chamber 40 causes the outer liner 14 to enlarge as shown in FIG. 8 because the interior thereof remains exposed to atmospheric pressure. While the outer liner is enlarged, the inner liner 12 is placed thereinto and the source of negative pressure is deactivated so that the outer liner 12 returns to its original shape and size, thereby closing tightly around the inner liner and adhering thereto when the adhesive cures.

The inner liner 12 is rolled onto a base member 13 (FIG. 8) preparatory to its insertion into the outer liner 14 by first rolling it inside out and then returning it to its initial configuration by unrolling it onto said base 13. Base 13 is mounted on a horizontal surface 15 and a passageway 17 admits ambient air at atmospheric pressure into the interior of the outer liner 14 as depicted in FIG. 8.

If the inner and outer liners share a common thickness, the bladder 32, when inflated, will deform symmetrically as depicted in FIG. 2. If the thickness of inner liner 12 is less than that of the outer liner, then the bladder will bulge more inwardly than outwardly; conversely, a thinner outer liner will result in an outward bulge greater than its inwardly extending counterpart. An inwardly directed bulge presses against the amputation stump, of course, whereas an outwardly directed bulge bears against the interior of the socket. Whether a symmetrical bulge as depicted in FIG. 2 or a nonsymmetrical bulge is employed is a matter for the discretion of the prosthetist. Similarly, the position, size, shape, and number of bladders 32 is similarly under the control of the prosthetist.

Figures 9, 10, 11:
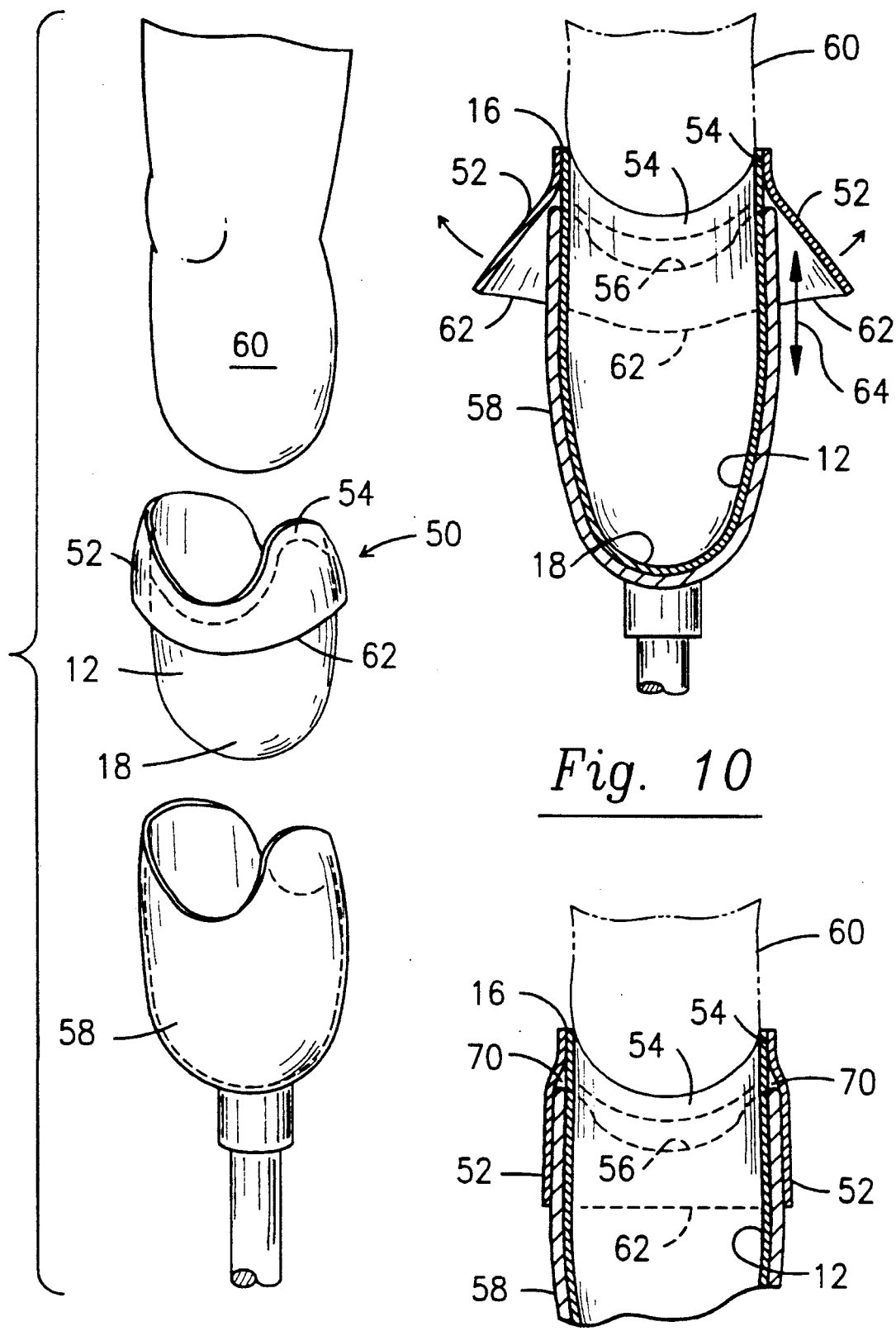
FIG. 9 is an exploded perspective view of a residual limb, the novel inner liner and cuff, and a socket having no check valve.
FIG. 10 is a front sectional view showing the inner liner fully received within the socket and the cuff pulled away from the inner liner to allow relative movement between said inner liner and said socket.
FIG. 11 is a view similar to FIG. 10, but showing the cuff in its position of repose.

Turning now to the second embodiment, reference is made to FIGS. 9–11.

In this embodiment, denoted 50 as a whole, outer liner 14 is not employed because no bladders are to be created. However, it should be noted that the outer liner of the first embodiment could also be used in connection with this second embodiment, either with or without bladders.

In this second embodiment, novel cuff 52 is provided. It, is a tubular member, i.e., it is open at its proximal and distal ends. It is made of the same elastomeric material as inner liner 12, and is glued to said inner liner by adhesive 54.

Note in FIGS. 9 and 10 that adhesive 54 is applied near the respective uppermost edges of liner 12 and cuff 52; note further in FIG. 10 that adhesive 54 is proximal to the uppermost rim 56 of socket 58 when the residual limb 60 is fully inserted into said socket 58.

FIG. 10 shows the lowermost edge 62 of cuff 52 pulled radially away from the inner liner 12 so that socket 58 may be inserted therebetween; clearly, adhesive 54 limits the depth of insertion of the socket into the space between the cuff 52 and the inner liner 12.

FIG. 11 shows the fully assembled apparatus, i.e., after the cuff 52 has been released so that its elasticity draws it back into tightly overlying relation to the outer surface of the socket 58 so that no air can enter into said socket. Note air pocket 70 that circumscribes the assembly. The first seal created by this novel assembly is between the inner surface of liner 12 and limb 60. The second seal is between the inner surface of cuff 52 and the outer surface of socket 58. The third seal that prevents air from escaping annular air pocket 70 is between the inner surface of cuff 52 and the outer surface of liner 12, said contact being just above air pocket 70 as shown in FIG. 11. When cuff 52 is pulled radially outwardly as shown in FIG. 10, liner 12 is easily slid into and out of socket 58 as indicated by double-headed directional arrow 64. Thus, it is very easy to attach the socket to the residual limb at the beginning of the day and to remove the residual limb from the socket at the end of the day.

This simple yet effective arrangement of parts eliminates the check valves, creams, and other expediencies that have been used for decades.

Note that it is a simple matter to combine the teachings of the first and second embodiments. Outer liner 14 may be provided in overlying relation to liner 12 in the embodiment of FIGS. 9–11 so that the bladders of the first embodiment may be provided, or cuff 52 may be added to the embodiment of FIGS. 1–8.

Turning now to the third embodiment, FIGS. 12–15, it should first be noted that the first and third embodiments may be used in conjunction with one another. However, the third embodiment supplants the second because it eliminates the separate cuff 52. The inner liner 12 is made sufficiently long so that the needed cuff means may be formed by simply rolling back the top part of said liner. As shown in FIG. 12, this creates an annular return bend as at 80. Moreover, it eliminates the need for any adhesive, because the liner and cuff are integrally formed with one another. However, a thin layer of adhesive 82 may still be applied as shown in FIG. 13. (It is also worth pointing out that the adhesive may also be eliminated in the second embodiment, because the cuff could be manufactured in such size that it would tightly overlie liner 12 in the absence of any adhesive means).

The one piece liner/cuff with or without adhesive may be used in all applications. When it is used in an application such as depicted in FIG. 11, a simple reverse folding of the type shown in FIGS. 12 and 13 will suffice. However, where the medial side of the prosthesis and the lateral side thereof are at different elevations, such as depicted in FIG. 14, it may be necessary to cut the liner 12 as at 84 in FIG. 15 and to place part 86 thereof into overlying relation to part 88 thereof, with a suitable application of adhesive, to take the slack from said liner that might otherwise appear. In such situations, an auxiliary cuff 90 (FIG. 14) might also be employed to further ensure that air pocket 70 (FIG. 11) retains its vacuum. Note that auxiliary cuff 90 completely encircles the folded back part of liner 12; the lower edge of the folded back part of said liner is shown in phantom lines FIG. 14.

Annular or toroidal air pocket 70, as above-mentioned, holds socket 58 on the residual limb 60 until the cuff is pulled out. Clearly, the operation of the inventive assembly relies on said air pocket; whether or not the cuff 52 and liner 12 are formed integrally with one another, or are formed separately and held together by adhesive means, or by press fit means, is inconsequential.

Those skilled in the art of prosthetics will note that liner 12 itself was never known heretofore, anywhere in the world. As mentioned earlier, it is preferably made of silicone. In a preferred embodiment, its sidewalls may be as thin as approximately 1/16" (about 1.5 mm), and it may be about ⅛" thick (about 3.0 mm) on the bottom thereof. In another embodiment, those respective thicknesses are doubled. The thickness should provide comfort to the individual wearing the liner. If the thickness is much less than about 1/16" (about 1.5 mm), then the material may also be subject to tearing.

This invention is clearly new and useful. Moreover, it was not obvious to those of ordinary skill in this art at the time it was made, in view of the prior art considered as a whole as required by law.

This invention pioneers the art of customized yet mass producible liners for prosthetic devices. Accordingly, the claims that follow are entitled to broad interpretation, as a matter of law, to protect from piracy the heart or essence of this breakthrough invention.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, What is claimed is:

1. An article of manufacture having utility in securing a rigid prosthesis socket to a residual limb, comprising:
   a liner made of elastomeric material adapted to be worn on the residual limb, said liner lining the socket when the residual limb is placed into said socket;
   a tubular cuff made of elastomeric material;
   said cuff disposed in overlying relation to said liner and having a predetermined diameter substantially equal to the predetermined diameter of said liner so that it tightly overlies said liner when in repose;
   said liner and said cuff being disposed in tightly abutting relation to one another along their respective uppermost edges;
   said socket having an uppermost end disposed in sandwiched relation to said cuff and liner; and
   an annular air pocket being disposed in circumscribing relation to said uppermost end of said socket;
   said annular air pocket forming a vacuum that circumscribes said uppermost end of said socket, said vacuum maintaining said socket between said cuff and said liner.

2. A method for securing a prosthesis socket to a residual limb, comprising the steps of:
   providing a liner to be worn on a residual limb and dimensioning said liner so that it lines the inner walls of said socket when the residual limb is fully inserted thereinto;
   providing a tubular cuff made of a resilient, elastomeric material that snugly overlies said liner in encircling relation thereto;
   attaching together said liner and said cuff along respective uppermost ends thereof;
   manually separating an unattached part of said cuff from said liner by pulling said unattached part of said cuff radially outwardly with respect to said liner;
   inserting an uppermost end of said socket between said liner and said cuff when said cuff is so separated;
   positioning said uppermost end of said socket in spaced relation to said respective uppermost ends of said liner and said cuff;
   forming a vacuum-creating annular air pocket that circumscribes the uppermost end of said socket and which retains said socket between said liner and said cuff by returning said cuff to its position of repose by releasing it so that it snugly overlies said socket.

3. An article of manufacture having utility in securing a rigid prosthesis socket to a residual limb, comprising:
   an elongate liner made of elastomeric resilient material adapted to be worn on the residual limb, said liner lining the socket when the residual limb is placed into said socket;
   said liner having an open upper end and a closed lower end;
   an annular return bend formed in said liner near said upper end;
   said annular return bend forming a cuff means, integral to said liner, said cuff means circumscribing and overlying said upper end of said liner;
   said socket having an upper end disposed in sandwiched relation between said liner and said cuff in spaced relation to said annular return bend;
   a vacuum-creating annular air pocket being formed in circumscribing relation to an uppermost end of said socket when said cuff means is in repose;
   said vacuum retaining said socket in said sandwiched relation.

4. The article of claim 3, further comprising a thin layer of adhesive disposed between an uppermost part of said liner and an uppermost part of said overlying integral cuff means.

5. The article of claim 3, further comprising a preselected cut made in said overlying integral cuff means, a thin layer of adhesive placed on a preselected part of said cuff adjacent said cut, and a first part of said cuff means disposed in overlying relation to said adhesive-covered preselected part, so that said integral cuff means may be advantageously used with a socket having its medial and lateral parts at differing elevations.

6. The article of claim 5, further comprising an auxiliary cuff disposed in encircling relation to said cuff means to further ensure that it stays in position on said socket.

7. The liner of claim 3, wherein said liner is an elastomeric member having a bag-like construction adapted to snugly fit over a residual limb;
   said member having side walls of predetermined thickness and an integral bottom wall having a predetermined thickness sufficient to provide comfort to the individual wearing said liner on said residual limb;
   said predetermined thickness of said side walls being about 1.5 mm–3.00 mm; and
   said predetermined thickness of said bottom wall being about 1.5 mm–6.00 mm.

8. The liner of claim 7, wherein said elastomeric material is silicone.

9. A method for securing a prosthesis socket to a residual limb, comprising the steps of:
   providing an elongate liner made of elastomeric resilient material that is worn on the residual limb and which lines the socket when the residual limb is placed thereinto;
   forming a return bend, in an upper part of said liner, that circumscribes said liner so that an integral cuff means is thereby created;
   manually pulling said cuff means away from said liner;
   inserting an upper end of said socket between said cuff means and said liner in closely spaced relation to said return bend; and
   forming a vacuum-creating annular pocket about an uppermost rim of said socket by releasing said cuff means so that its resiliency causes it to overlie said socket;
   said vacuum retaining said socket between said liner and said cuff.

10. The method of claim 7, further comprising the step of placing a thin layer of adhesive between an uppermost part of said liner and an uppermost part of said cuff means.

11. The method of claim 10, further comprising the step of making a cut in said cuff means, placing a thin layer of adhesive on said cuff means adjacent said cut, and placing a first part of said cuff means in overlying relation to said adhesive-covered part thereof so that said liner may be fitted to a socket having its medial and lateral parts at differing elevations.

12. The method of claim 11, further comprising the step of positioning an auxiliary cuff in encircling relation to said cuff means to further hold said cuff means to said socket.

* * * * *